US010603098B2

(12) United States Patent
Mattmiller et al.

(10) Patent No.: US 10,603,098 B2
(45) **Date of Patent: *Mar. 31, 2020**

(54) GAIN COMPENSATION FOR A FULL BRIDGE INVERTER

(71) Applicant: COVIDIEN LP, Mansfield, MA (US)

(72) Inventors: Aaron Mattmiller, Longmont, CO (US); Donald Tonn, Superior, CO (US); Alexander M. Waskiewicz, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 715 days.

This patent is subject to a terminal disclaimer.

(21) Appl. No.: 15/349,646

(22) Filed: Nov. 11, 2016

(65) Prior Publication Data

US 2017/0056092 A1 Mar. 2, 2017

Related U.S. Application Data

(63) Continuation of application No. 14/168,296, filed on Jan. 30, 2014, now Pat. No. 9,504,516.

(Continued)

(51) Int. Cl.

| | |
|---|---|
| ***A61B 18/12*** | (2006.01) |
| *A61B 18/00* | (2006.01) |

(52) U.S. Cl.

CPC .. *A61B 18/1206* (2013.01); *A61B 2018/0075* (2013.01); *A61B 2018/00642* (2013.01);

(Continued)

(58) Field of Classification Search

CPC ...... A61B 18/1206; A61B 2018/00642; A61B 2018/00702; A61B 2018/00726;

(Continued)

(56) References Cited

U.S. PATENT DOCUMENTS

| | | |
|---|---|---|
| 3,601,126 A | 8/1971 | Estes |
| 3,683,923 A | 8/1972 | Anderson |

(Continued)

FOREIGN PATENT DOCUMENTS

| | | |
|---|---|---|
| CN | 2777841 Y | 5/2006 |
| CN | 102307020 A | 1/2012 |

(Continued)

OTHER PUBLICATIONS

Chinese Office Action and English translation issued in Appl. No. CN 201410138870.5 dated Jul. 4, 2017.

(Continued)

*Primary Examiner* — Jaymi E Della

(74) *Attorney, Agent, or Firm* — Carter, DeLuca & Farrell LLP

(57) ABSTRACT

An electrosurgical generator includes a gain-compensated full bridge topology. Gain nonlinearity is corrected by applying impedance and phase correction factors to a control loop to achieve a linear gain structure. In embodiments, gain compensation is performed by comparing an RF setpoint signal with a calculated output signal to generate a first error signal. An impedance correction factor is applied to the first error signal to generate a second error signal. The second error signal is processed by a proportional-integral-derivative controller to generate a phase control signal. A phase control correction factor is applied to the phase control signal to generate a corrected pulse width modulation driving signal, which is used to generate PWM driving signals for a full-bridge inverter. One or more sensors provide feedback for comparison with the RF setpoint.

20 Claims, 10 Drawing Sheets

Related U.S. Application Data

(60) Provisional application No. 61/829,433, filed on May 31, 2013.

(52) U.S. Cl.
CPC ............... *A61B 2018/00702* (2013.01); *A61B 2018/00726* (2013.01); *A61B 2018/00827* (2013.01); *A61B 2018/00875* (2013.01); *A61B 2018/00892* (2013.01); *A61B 2018/1286* (2013.01)

(58) Field of Classification Search
CPC .. A61B 2018/0075; A61B 2018/00827; A61B 2018/00875; A61B 2018/00892; A61B 2018/1286
See application file for complete search history.

(56) References Cited

U.S. PATENT DOCUMENTS 3,826,263 A 7/1974 Cage et al.
3,887,861 A 6/1975 Anzai et al.
3,964,487 A 6/1976 Judson
3,978,393 A 8/1976 Wisner et al.
3,980,085 A 9/1976 Ikuno
4,092,986 A 6/1978 Schneiderman
4,126,137 A 11/1978 Archibald
4,188,927 A 2/1980 Harris
4,281,373 A 7/1981 Mabille
4,287,557 A 9/1981 Brehse
4,524,444 A 6/1985 Efron et al.
4,586,120 A 4/1986 Malik et al.
4,590,934 A 5/1986 Malis et al.
4,658,819 A 4/1987 Harris et al.
4,727,874 A 3/1988 Bowers et al.
4,887,199 A 12/1989 Whittle
4,961,047 A 10/1990 Carder
5,099,840 A 3/1992 Goble et al.
5,113,116 A 5/1992 Wilson
5,216,338 A 6/1993 Wilson
5,396,194 A 3/1995 Williamson et al.
5,414,238 A 5/1995 Steigerwald et al.
5,498,261 A 3/1996 Strul
5,531,774 A 7/1996 Schulman et al.
5,559,688 A 9/1996 Pringle
5,678,568 A 10/1997 Uchikubo et al.
5,702,386 A 12/1997 Stern et al.
5,729,448 A 3/1998 Haynie et al.
5,755,715 A 5/1998 Stern et al.
5,906,614 A 5/1999 Stern et al.
6,123,702 A 9/2000 Swanson et al.
6,162,217 A 12/2000 Kannenberg et al.
6,183,468 B1 2/2001 Swanson et al.
6,245,065 B1 6/2001 Panescu et al.
6,409,722 B1 6/2002 Hoey et al.
6,494,880 B1 12/2002 Swanson et al.
6,537,272 B2 3/2003 Christopherson et al.
6,693,782 B1 2/2004 Lash
6,696,844 B2 2/2004 Wong et al.
6,733,495 B1 5/2004 Bek et al.
6,736,810 B2 5/2004 Hoey et al.
6,740,079 B1 5/2004 Eggers et al.
6,740,085 B2 5/2004 Hareyama et al.
6,849,073 B2 2/2005 Hoey et al.
6,939,346 B2 9/2005 Kannenberg et al.
6,942,660 B2 9/2005 Pantera et al.
6,974,463 B2 12/2005 Magers et al.
7,041,096 B2 5/2006 Malis et al.
7,058,372 B1 6/2006 Pardoen et al.
7,062,331 B2 6/2006 Zarinetchi et al.
7,169,144 B2 1/2007 Hoey et al.
7,190,933 B2 3/2007 De Ruijter et al.
7,203,556 B2 4/2007 Daners
7,247,155 B2 7/2007 Hoey et al.
7,250,746 B2 7/2007 Oswald et al.
7,269,034 B2 9/2007 Schlecht
7,294,127 B2 11/2007 Leung et al.
7,396,336 B2 7/2008 Orszulak et al.
D574,323 S 8/2008 Waaler
7,468,499 B2 12/2008 Canini et al.
7,511,472 B1 3/2009 Xia et al.
7,582,084 B2 9/2009 Swanson et al.
7,655,003 B2 2/2010 Lorang et al.
7,722,601 B2 5/2010 Wham et al.
7,736,358 B2 6/2010 Shores et al.
7,799,020 B2 9/2010 Shores et al.
7,863,841 B2 1/2011 Menegoli et al.
8,012,150 B2 9/2011 Wham et al.
8,045,943 B2 10/2011 Kaczman et al.
8,080,008 B2 12/2011 Wham et al.
8,096,961 B2 1/2012 Orszulak et al.
8,113,057 B2 2/2012 Orszulak et al.
8,267,929 B2 9/2012 Wham et al.
8,287,529 B2 10/2012 Orszulak
8,298,223 B2 10/2012 Wham et al.
8,303,580 B2 11/2012 Wham et al.
8,377,053 B2 2/2013 Orszulak
8,485,993 B2 7/2013 Orszulak et al.
9,504,516 B2 11/2016 Mattmiller et al.
2003/0199863 A1 10/2003 Swanson et al.
2004/0172016 A1 9/2004 Bek et al.
2005/0004564 A1 1/2005 Wham et al.
2005/0190583 A1 9/2005 Morimoto et al.
2006/0161148 A1* 7/2006 Behnke ............. A61B 18/1206
606/34
2006/0224151 A1 10/2006 Waaler
2006/0293649 A1 12/2006 Lorang et al.
2007/0093800 A1 4/2007 Wham et al.
2007/0093801 A1 4/2007 Behnke
2008/0015563 A1 1/2008 Hoey et al.
2008/0015564 A1 1/2008 Wham et al.
2008/0082095 A1 4/2008 Shores et al.
2008/0082096 A1 4/2008 Shores et al.
2008/0287791 A1 11/2008 Orszulak et al.
2008/0287838 A1 11/2008 Orszulak et al.
2009/0030477 A1 1/2009 Jarrard
2010/0063494 A1 3/2010 Orszulak
2010/0063497 A1 3/2010 Orszulak
2010/0121318 A1 5/2010 Hancock et al.
2010/0168730 A1 7/2010 Hancock et al.
2010/0191233 A1 7/2010 Wham et al.
2010/0211063 A1 8/2010 Wham et al.
2010/0268220 A1 10/2010 Johnson et al.
2011/0068828 A1 3/2011 Anderson et al.
2011/0087213 A1 4/2011 Messerly et al.
2012/0089139 A1 4/2012 Wham et al.
2012/0116268 A1 5/2012 Orszulak et al.
2012/0239026 A1 9/2012 Orszulak et al.
2012/0265195 A1 10/2012 Gilbert
2013/0023869 A1 1/2013 Orszulak
2013/0035679 A1 2/2013 Orszulak
2013/0066311 A1 3/2013 Smith et al.
2013/0079763 A1 3/2013 Heckel et al.
2013/0158541 A1 6/2013 Orszulak
2013/0325380 A1 12/2013 Behnke, II et al.
2014/0039490 A1 2/2014 Wham
2014/0043070 A1 2/2014 Gilbert
2014/0058381 A1 2/2014 Wham et al.
2014/0058385 A1 2/2014 Wham et al.
2014/0062593 A1 3/2014 Gilbert
2014/0094796 A1 4/2014 Behnke, II
2014/0100559 A1 4/2014 Wham et al.
2014/0114303 A1 4/2014 Johnston

FOREIGN PATENT DOCUMENTS

DE 179607 C 3/1905
DE 390937 C 3/1924
DE 1099658 B 2/1961
DE 1139927 B 11/1962
DE 1149832 B 6/1963
DE 1439302 A1 1/1969
DE 2439587 A1 2/1975
DE 2455174 A1 5/1975

(56) References Cited

FOREIGN PATENT DOCUMENTS

| | | | |
|---|---|---|---|
| DE | 2407559 | A1 | 8/1975 |
| DE | 2602517 | A1 | 7/1976 |
| DE | 2504280 | A1 | 8/1976 |
| DE | 2540968 | A1 | 3/1977 |
| DE | 2820908 | A1 | 11/1978 |
| DE | 2803275 | A1 | 8/1979 |
| DE | 2823291 | A1 | 11/1979 |
| DE | 2946728 | A1 | 5/1981 |
| DE | 3143421 | A1 | 5/1982 |
| DE | 3045996 | A1 | 7/1982 |
| DE | 3120102 | A1 | 12/1982 |
| DE | 3510586 | A1 | 10/1986 |
| DE | 3604823 | A1 | 8/1987 |
| DE | 3904558 | A1 | 8/1990 |
| DE | 3942998 | A1 | 7/1991 |
| DE | 4206433 | A1 | 9/1993 |
| DE | 4339049 | A1 | 5/1995 |
| DE | 19506363 | A1 | 8/1996 |
| DE | 19717411 | A1 | 11/1998 |
| DE | 19848540 | A1 | 5/2000 |
| DE | 102008058737 | A1 | 4/2010 |
| EP | 0246350 | A1 | 11/1987 |
| EP | 267403 | A2 | 5/1988 |
| EP | 296777 | A2 | 12/1988 |
| EP | 310431 | A2 | 4/1989 |
| EP | 325456 | A2 | 7/1989 |
| EP | 336742 | A2 | 10/1989 |
| EP | 390937 | A1 | 10/1990 |
| EP | 0556705 | A1 | 8/1993 |
| EP | 608609 | A2 | 8/1994 |
| EP | 0836868 | A2 | 4/1998 |
| EP | 080220 | A2 | 11/1998 |
| EP | 0882955 | A1 | 12/1998 |
| EP | 1051948 | A2 | 11/2000 |
| EP | 1263181 | A1 | 12/2002 |
| EP | 1366724 | A1 | 12/2003 |
| EP | 1681026 | A2 | 7/2006 |
| EP | 1776929 | A1 | 4/2007 |
| EP | 2393208 | A2 | 12/2011 |
| FR | 1275415 | A | 11/1961 |
| FR | 1347865 | A | 1/1964 |
| FR | 2313708 | A1 | 12/1976 |
| FR | 2364461 | A1 | 4/1978 |
| FR | 2502935 | A1 | 10/1982 |
| FR | 2517953 | A1 | 6/1983 |
| FR | 2573301 | A1 | 5/1986 |
| GB | 2164473 | A | 3/1986 |
| GB | 2214430 | A | 9/1989 |
| JP | 63005876 | | 1/1988 |
| JP | 2002065690 | A | 3/2002 |
| JP | 2005185657 | A | 7/2005 |
| SU | 166452 | | 11/1964 |
| SU | 727201 | A2 | 4/1980 |
| WO | 0211634 | A1 | 2/2002 |
| WO | 0232333 | A1 | 4/2002 |
| WO | 0245589 | A2 | 6/2002 |
| WO | 03047446 | A1 | 6/2003 |
| WO | 03090635 | A1 | 11/2003 |
| WO | 2004098385 | A2 | 11/2004 |
| WO | 2006050888 | A1 | 5/2006 |
| WO | 2008043999 | A2 | 4/2008 |
| WO | 2008053532 | A1 | 5/2008 |
| WO | 2008071914 | A2 | 6/2008 |
| WO | 2008110756 | A2 | 9/2008 |

OTHER PUBLICATIONS

European Search Report No. 14166165.2 dated Jul. 8, 2014.

Wald et al., "Accidental Burns", JAMA, Aug. 16, 1971, vol. 217, No. 7, pp. 916-921.

Vallfors et al., "Automatically Controlled Bipolar Electrosoagulation—'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944, pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843. cited byapplicant.

Muller et al. "Extended Left Hemicolectomy Using the LigaSure Vessel Sealing System", Innovations That Work; Company Newsletter; Sep. 1999.

Ogden Goertzel Alternative to the Fourier Transform: Jun. 1993 pp. 485-487, Electronics World; Reed Business Publishing, Sutton, Surrey, BG vol. 99, No. 9, 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with computerized Tomography to Enhance Spatial Accuracy", Journal Neurosurgery, 83; (1995) pp. 271-276.

Geddes et al., "The Measurement of Physiologic Events by Electrical Impedence", Am. J. Ml, Jan. Mar. 1964, pp. 16-27.

Cosman et al., "Methods of Making Nervous System Lesions", In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-Of-Flight and Absorbance Imaging of Biologic Media", Science, American Association for be Advancement of Science, Washington, DC, vol. 259, Mar. 5, 1993, pp. 1463-1466.

Cosman et al., "Radiofrequency Lesion Generation and Its Effect on Tissue Impedance", Applied Neurophysiology 51:(1988) pp. 230-242.

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297, Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone", Neurosurgery 15: (1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300", 1 p. Sep. 1998.

Valleylab Brochure "Valleylab Electroshield Monitoring System", 2 pp. Nov. 1995.

"Electrosurgical Unit Analyzer ESU-2400 Series User Manual" Apr. 1, 2002; Retrieved from Internet: <URL:http://www.bcgroupintl.com/ESU.sub.--2400/Updates/ESU-2400.sub.—UM.sub.—Rev04.pdf>, pp. 6, 11, 73.

U.S. Appl. No. 10/406,690, filed Apr. 3, 2003 inventor: Behnke.

U.S. Appl. No. 10/573,713, filed Mar. 28, 2006 inventor: Wham.

(56) References Cited

OTHER PUBLICATIONS

U.S. Appl. No. 10/761,524, filed Jan. 21, 2004 inventor: Wham.
U.S. Appl. No. 11/242,458, filed Oct. 3, 2005 inventor: Becker.
U.S. Appl. No. 13/943,518, filed Jul. 16, 2013 inventor: Orszulak et al.
U.S. Appl. No. 14/069,534, filed Nov. 1, 2013 inventor: Digmann.
U.S. Appl. No. 14/096,341, filed Dec. 4, 2013 inventor: Johnson.
U.S. Appl. No. 14/098,859, filed Dec. 6, 2013 inventor: Johnson.
U.S. Appl. No. 14/100,113, filed Dec. 9, 2013 inventor: Gilbert.
U.S. Appl. No. 14/147,294, filed Jan. 3, 2014 inventor: Gilbert.
U.S. Appl. No. 14/147,312, filed Jan. 3, 2014 inventor: Gilbert.
U.S. Appl. No. 14/174,551, filed Feb. 6, 2014 inventor: Johnson.
U.S. Appl. No. 14/174,607, filed Feb. 6, 2014 inventor: Friedrichs.
U.S. Appl. No. 14/179,724, filed Feb. 13, 2014 inventor: Johnson.
U.S. Appl. No. 14/180,965, filed Feb. 14, 2014 inventor: Larson.
U.S. Appl. No. 14/181,114, filed Feb. 14, 2014 inventor: Larson.
U.S. Appl. No. 14/182,797, filed Feb. 18, 2014 inventor: Wham.
U.S. Appl. No. 14/183,196, filed Feb. 18, 2014 inventor: Krapohl.
U.S. Appl. No. 14/190,830, filed Feb. 26, 2014 inventor: Johnson.
U.S. Appl. No. 14/190,895, filed Feb. 26, 2014 inventor: Gilbert.
U.S. Appl. No. 14/192,112, filed Feb. 27, 2014 inventor: Weinberg.
U.S. Appl. No. 14/255,051, filed Apr. 17, 2014 inventor: Coulson.
European Examination Report from EP Appl. No. 14166165.2 dated Apr. 21, 2016.

* cited by examiner

GAIN COMPENSATION FOR A FULL BRIDGE INVERTER

CROSS REFERENCE TO RELATED APPLICATION

The present application is a continuation of U.S. application Ser. No. 14/168,296, filed on Jan. 30, 2014, which claims the benefit of and priority to U.S. Provisional Application Ser. No. 61/829,433, filed on May 31, 2013. The entire disclosures of all of the foregoing applications are incorporated by reference herein.

BACKGROUND

1. Technical Field

The present disclosure is directed to electrosurgical systems, and, in particular, to a circuit and method for achieving gain compensation across varying operating conditions in an electrosurgical generator utilizing a full bridge topology.

2. Description of the Related Art

An electrosurgical generator is used in surgical procedures to deliver electrical energy to the tissue of a patient. When an electrode is connected to the generator, the electrode can be used for cutting, coagulating or sealing the tissue of a patient with high frequency electrical energy. During normal operation, alternating electrical current from the generator flows between an active electrode and a return electrode by passing through the tissue and bodily fluids of a patient.

The electrical energy usually has its waveform shaped to enhance its ability to cut, coagulate or seal tissue. Different waveforms correspond to different modes of operation of the generator, and each mode gives the surgeon various operating advantages. Modes may include cut, coagulate, a blend thereof, desiccate, seal, or spray. A surgeon can easily select and change the different modes of operation as the surgical procedure progresses.

In each mode of operation, it is important to regulate the electrosurgical energy delivered to the patient to achieve the desired surgical effect. Applying more than the correct dosage may result in tissue destruction, and may prolong healing. Applying less than the desired dosage of energy power inhibits the surgical procedure. Thus, it is desirable to control the output energy from the electrosurgical generator for the type of tissue being treated.

Different types of tissues will be encountered as the surgical procedure progresses and each unique tissue requires more or less power as a function of frequently changing tissue impedance. As different types of tissue and bodily fluids are encountered, the impedance changes and the response time of the electrosurgical control of output power must be rapid enough to seamlessly permit the surgeon to treat the tissue. Moreover, the same tissue type can be desiccated during electrosurgical treatment and thus its impedance will change dramatically in the space of a very brief time. The electrosurgical output power control has to respond to such impedance changes as well.

Three standard modes of control are commonly used during electrosurgical generation. At low tissue impedances, the generator controls to a current limit. At mid-range tissue impedances, the generator controls to a power limit. At highest tissue impedances, the generator controls to a voltage limit. Generally, the voltage, current, and power limits describe the electrosurgical mode. The generator must employ a stable control loop over the full impedance range whether controlling to voltage, current, or power.

In prior-art electrosurgical generator designs, voltage from the AC mains is rectified to provide a DC voltage. An inverter stage converts the DC voltage back to AC voltages at frequencies appropriate for the desired tissue effect. The output of this stage is an AC waveform that can be controlled to voltage, current, or power, to deliver the correct energy to tissue.

A common technique for configuring a variable DC power supply utilizes Phase Shifted Full Bridge topology wherein output power is controlled via changes in the duty cycle of a pulse-width modulated input signal. At any single operating point, the gain of a phase shifted full-wave bridge inverter is linear. However, the operating points may vary over a wide range due to a setpoint change, a load change, an impedance change, and changes in other parameters. Consequently, the overall gain of the inverter stage can vary significantly. This can have an impact on the controlled delivery of energy to tissue.

SUMMARY

Disclosed is a system for controlling an electrosurgical generator using a gain-compensated full bridge topology. In embodiments, the disclosed system includes a summation unit configured to receive an RF setpoint signal and a calculated output signal, and to generate a first error signal corresponding to the difference between the RF setpoint signal and the calculated output signal. An impedance gain compensation unit in operable communication with the summation unit is configured to receive the first error signal and an impedance signal corresponding to the load impedance, and to generate a second error signal in accordance with an impedance correction calculation. A compensator in operable communication with the impedance gain compensation unit receives the second error signal and generates a phase control signal. In embodiments, the compensator includes a proportional-integral-derivative (PID) controller.

The system includes a phase gain compensation unit having a phase preprocessing module that is configured to receive the phase control signal, apply a phase gain correction function to the phase control signal to generate a corrected pulse width modulation driving signal. The phase gain compensation unit includes a pulse width modulation driver configured to generate a first full bridge driving signal and a second full bridge driving signal. The second full bridge driving signal is shifted in phase from the first full bridge driving signal by an amount corresponding to the corrected pulse width modulation driving signal. A full bridge inverter in operable communication with the pulse width modulation driver receives the first full bridge driving signal and the second full bridge driving signal, and generates an electrosurgical output signal having an electrical property corresponding to a difference in phase between the first full bridge driving signal and the second full bridge driving signal. The system includes a sensor circuit configured to sense an electrical property of the electrosurgical output signal and generate a corresponding calculated output signal. The electrical property may include, without limitation, an output voltage, an output current, an output power, or an output impedance.

In embodiments, the phase control circuit includes a clock configured to generate the first full bridge driving signal. The clock is disposed in operative communication with at least one of the pulse width modulation driver and the full-bridge inverter.

In embodiments, the sensor circuit includes one or more sensors operably associated with an output of the full-bridge inverter and configured to output a sensor signal having a first format. The sensor circuit includes a sensor unit in operable communication with the one or more sensors and configured to receive the sensor signal, convert the sensor signal from the first format into a second format, and outputting the sensor signal in the second format. In embodiments, the first format may be an analog format and the second format may be a digital format. A parameter calculation unit is configured to receive the sensor signal in the second format, and compute a calculated output signal in accordance with an operating mode of the electrosurgical generator. In embodiments, the operating mode of the electrosurgical generator is selected from the group consisting of a voltage-targeted mode, a current-targeted mode, a power-targeted mode, and an impedance-targeted mode.

In embodiments, the full bridge inverter includes a resonant network configured to provide a generally sinusoidal electrosurgical output waveform. In embodiments, the resonant network includes a bandpass filter.

In embodiments, the phase gain correction function is performed in accordance with an arcsine function.

In embodiments, the steady state output of a full bridge inverter in a voltage-targeted mode in accordance with the present disclosure, wherein a phase shifted square wave is well-filtered over a band pass network such that the Fourier fundamental is the dominant harmonic, may be determined in accordance with the formula $$|V_{out}| = \frac{4V_g}{\pi}\sin\frac{\theta_{12}}{2} * |H_v|,$$

where $H_v$ is the voltage transfer function of the resonant tank in combination with the load.

In embodiments, the steady state output of a full bridge inverter in a current-targeted mode in accordance with the present disclosure, wherein a phase shifted square wave is well-filtered over a band pass network such that the Fourier fundamental is the dominant harmonic, may be determined in accordance with the formula $$|I_{out}| = \frac{4V_g}{\pi}\sin\frac{\theta_{12}}{2} * \frac{|H_v|}{R_{LOAD}}.$$

In embodiments, the steady state output of a full bridge inverter in a power-targeted mode in accordance with the present disclosure, wherein a phase shifted square wave is well-filtered over a band pass network such that the Fourier fundamental is the dominant harmonic, may be determined in accordance with the formula $$|P_{out}| = \frac{\left(\frac{4V_g}{\pi}\sin\frac{\theta_{12}}{2} * |H_v|\right)^2}{R_{LOAD}}.$$

In embodiments, when the electrosurgical generator is in a current-targeted operating mode the impedance correction calculation is performed in accordance with the formula $$\text{abs}\left(\frac{R_{LOAD} + Z_{o0}}{1}\right).$$

In embodiments, when the electrosurgical generator is in a power-targeted operating mode the impedance correction calculation is performed in accordance with the formula $$\text{abs}\left(\frac{(R_{LOAD} + Z_{o0})^2}{R_{LOAD}}\right).$$

In embodiments, when the electrosurgical generator is in a voltage-targeted operating mode the impedance correction calculation is performed in accordance with the formula $$\text{abs}\left(\frac{R_{LOAD} + Z_{o0}}{R_{LOAD}}\right),$$

where $Z_{o0}$ is the Thevenin equivalent output impedance of the resonant network (e.g., reactive).

Also disclosed is a method for performing gain compensation in an electrosurgical generator. The method includes the steps of receiving an RF setpoint signal and a calculated output signal, generating a first error signal corresponding to the difference between the RF setpoint signal and the calculated output signal, generating a second error signal by applying an impedance correction calculation to the first error signal, generating a phase control signal with a proportional-integral-derivative controller, applying a phase gain correction function to the phase control signal to generate a corrected pulse width modulation driving signal, generating a first full bridge driving signal, and generating a second full bridge driving signal that is shifted in phase from the first full bridge driving signal by an amount corresponding to the corrected pulse width modulation driving signal.

In embodiments, the phase gain correction function is performed in accordance with an arcsine function.

In embodiments, the phase gain correction function is performed in accordance with an arcsine function when controlling to voltage or current.

In embodiments, the phase gain correction function is performed by squaring the compensator output and subsequently employing an arcsine function when controlling to power.

In embodiments, the disclosed method includes the steps of generating an electrosurgical output signal having an electrical property corresponding to a difference in phase between the first full bridge driving signal and the second full bridge driving signal. In embodiments, the disclosed method includes sensing an electrical property of the electrosurgical output signal and generating a calculated output signal corresponding to the electrosurgical output signal. In embodiments, the disclosed method includes converting the sensed electrical property from a first format into a second format. In embodiments, the calculated output signal is generated in accordance with an operating mode of the electrosurgical generator.

In embodiments of the disclosed method, when the electrosurgical generator is in a voltage-targeted mode the impedance correction calculation is performed in accordance with the formula $$\text{abs}\left(\frac{R_{LOAD} + Z_{o0}}{R_{LOAD}}\right),$$

where $Z_{o0}$ is the Thevenin equivalent output impedance of the resonant network and is reactive.

In embodiments of the disclosed method, when the electrosurgical generator is in a current-targeted mode the impedance correction calculation is performed in accordance with the formula $$\text{abs}\left(\frac{R_{LOAD}+Z_{o0}}{1}\right).$$

In embodiments of the disclosed method, when the electrosurgical generator is in a power-targeted mode the impedance correction calculation is performed in accordance with the formula $$\text{abs}\left(\frac{(R_{LOAD}+Z_{o0})^2}{R_{LOAD}}\right).$$

Also disclosed is an electrosurgical generator. In embodiments, the electrosurgical generator includes a controller configured to receive an operational parameter from a user interface, a user interface in operable communication with the controller and configured to receive a user input from a user, and a gain-compensated radiofrequency stage. The gain-compensated radiofrequency stage includes a summation unit configured to receive an RF setpoint signal and a calculated output signal, and to generate a first error signal corresponding to the difference between the RF setpoint signal and the calculated output signal. The gain-compensated inverter stage includes an impedance gain compensation unit configured to receive the first error signal and an impedance signal corresponding to the load impedance, and to generate a second error signal in accordance with an impedance correction calculation. The gain-compensated radiofrequency stage includes a compensator which receives the second error signal and generates a phase control signal. In embodiments, the compensator includes a proportional-integral-derivative controller.

The gain-compensated inverter stage includes a phase gain compensation unit. The phase gain compensation unit includes a phase preprocessing module that is configured to receive the phase control signal, apply phase change correction function to the phase control signal to generate a corrected pulse width modulation driving signal. The phase gain compensation unit further includes a pulse width modulation driver configured to generate a first full bridge driving signal, and a second full bridge driving signal that is shifted in phase from the first full bridge driving signal by an amount corresponding to the corrected pulse width modulation driving signal.

The inverter stage includes a full bridge inverter and a resonant network configured to receive the first full bridge driving signal and the second full bridge driving signal, and generate an electrosurgical output signal having an electrical property corresponding to the difference in phase between the first full bridge driving signal and the second full bridge driving signal. The gain-compensated inverter stage includes a sensor circuit configured to sense an electrical property of the electrosurgical output signal and generate a corresponding calculated output signal. The electrical property may include, without limitation, an output voltage, an output current, an output power, or an output impedance.

In embodiments, the sensor circuit of the electrosurgical generator includes one or more sensors operably associated with an output of the full-bridge inverter and configured to output a sensor signal having a first format. The sensor circuit includes a sensor unit in operable communication with the one or more sensors and configured to receive the sensor signal, convert the sensor signal from the first format into a second format, and outputting the sensor signal in the second format. The sensor circuit includes a parameter calculation unit configured to receive the sensor signal in the second format and compute a calculated output signal in accordance with an operating mode of the electrosurgical generator.

In embodiments of the electrosurgical generator, the phase gain correction function is performed in accordance with an arcsine function.

In embodiments of the electrosurgical generator, the phase gain correction function is performed in accordance with an arcsine function when performing voltage and/or current compensation.

In embodiments of the electrosurgical generator, the phase gain correction function is performed by squaring the compensator output and subsequently employing an arcsine function when performing power compensation.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
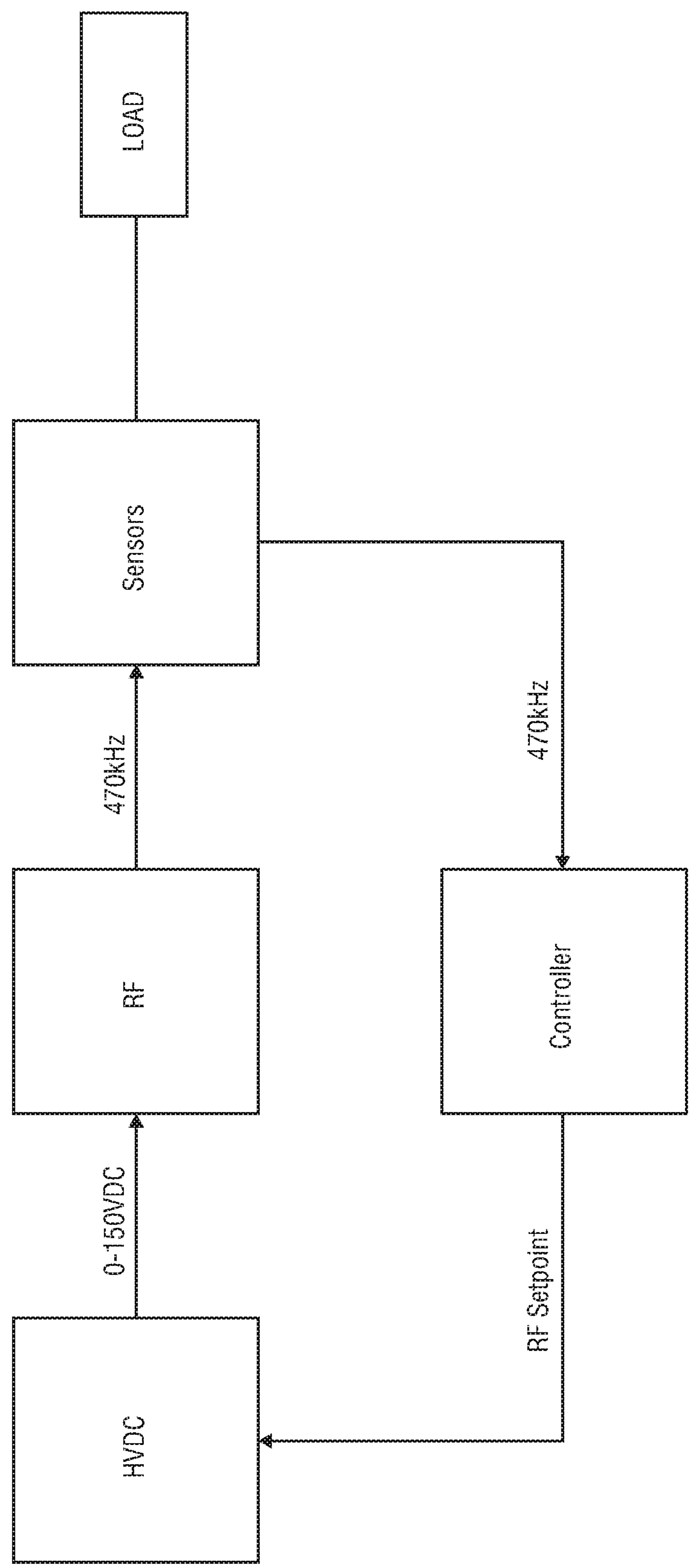
FIG. 1 is a block diagram of a prior-art electrosurgical generator.

Embodiments of the present disclosure are described herein below with reference to the accompanying drawings. In the following description, well-known functions or constructions are not described in detail to avoid obscuring the invention in unnecessary detail. In the Figures, like reference numerals represent like elements.

Additionally, embodiment in accordance with the present disclosure may be described herein in terms of functional block components and various processing steps. It should be appreciated that such functional blocks may be realized by any number of hardware and/or software components configured to perform the specified functions. For example, embodiments of the present disclosure may employ various integrated circuit components, e.g., memory elements, processing elements, logic elements, and the like, which may carry out a variety of functions under the control of one or more microprocessors or other control devices. Accordingly, functional blocks of the block diagrams support combinations of manners for performing the specified functions, combinations of steps for performing the specified functions, and program instructions for performing the specified functions. It will also be understood that each functional block of the block diagrams, and combinations of functional blocks in the block diagrams, can be implemented by either special purpose hardware-based systems that perform the specified functions or steps, or suitable combinations of special purpose hardware and software instructions.

In a prior-art electrosurgical generator arrangement as shown in FIG. 1, a high voltage DC power source (HVDC) provides a supply voltage that is variable from 0-150 VDC to an RF generator stage in accordance with an RF setpoint signal. The RF generator stage generates a 470 kHz electrosurgical signal having an output power determined by the supply voltage. One or more sensors monitor the output of the RF generator as applied to a load, such as to targeted tissue of a patent. The sensors provide a feedback signal to a controller. The controller is programmed to cause the RF generator stage to generate a desired RF output signal in accordance with inputs received from a surgeon. The desired RF output signal may include particular power, waveform, and modulations selected to achieve a specific surgical objective such as cutting, sealing, coagulating, blending, and so forth. The controller processes the feedback signal in view of the desired RF output signal and turn provides the appropriate RF setpoint signal to the HVDC to achieve the desired output signal. This arrangement may have drawbacks, since the output of the RF stage may be non-linear with respect to the variable supply voltage input, and may also exhibit inefficiencies and instabilities at certain operating points.

Figure 2:
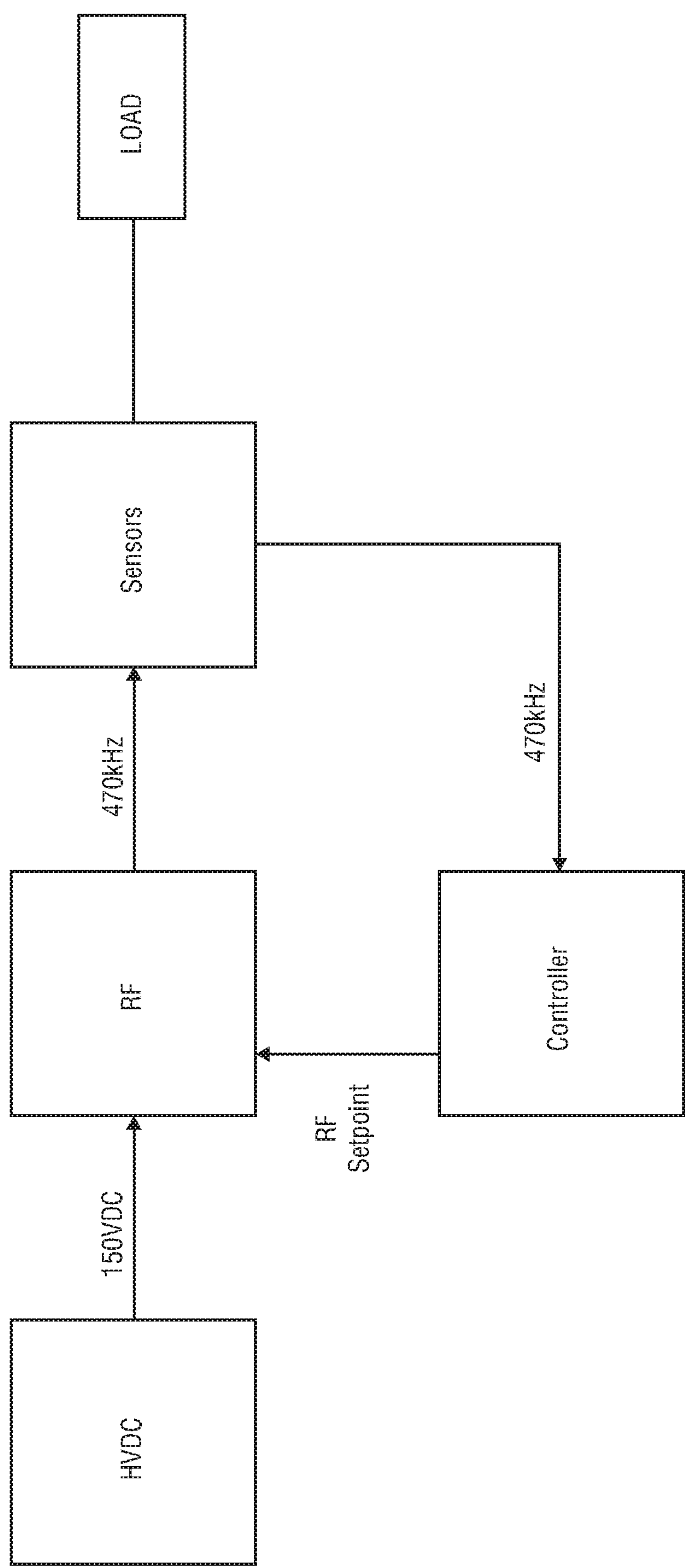
FIG. 2 is a block diagram of another prior-art electrosurgical generator.

In another prior-art electrosurgical generator arrangement shown in FIG. 2, an HVDC provides a fixed DC supply voltage of to the RF generator stage. The RF inverter is configured to operate at this fixed supply voltage and includes an RF setpoint input. The RF generator stage generates an high-frequency (e.g., 470 kHz) AC electrosurgical signal having an output determined by the RF setpoint input. This arrangement is said to have advantages over the FIG. 1 arrangement in that the system response time and operating efficiencies are improved.

Both the FIG. 1 and FIG. 2 arrangements may have drawbacks in that, as the operating point changes, either through a setpoint change or a load change, the gain exhibited by the system can vary significantly. Prior art solutions to the gain problem typically involve controlling a gain compensator based on known operating point data. A cross-reference of compensation factors and operating points is created by measuring the generator gain throughout an anticipated range of operating points and operation modes, which is then stored in a large three-dimensional lookup table for use during electrosurgical procedures. However, such approaches may have drawbacks, since the lookup tables are difficult to implement, are generally device-specific, and require extensive reprogramming if even a single element of the system is changed.

Figure 3A:
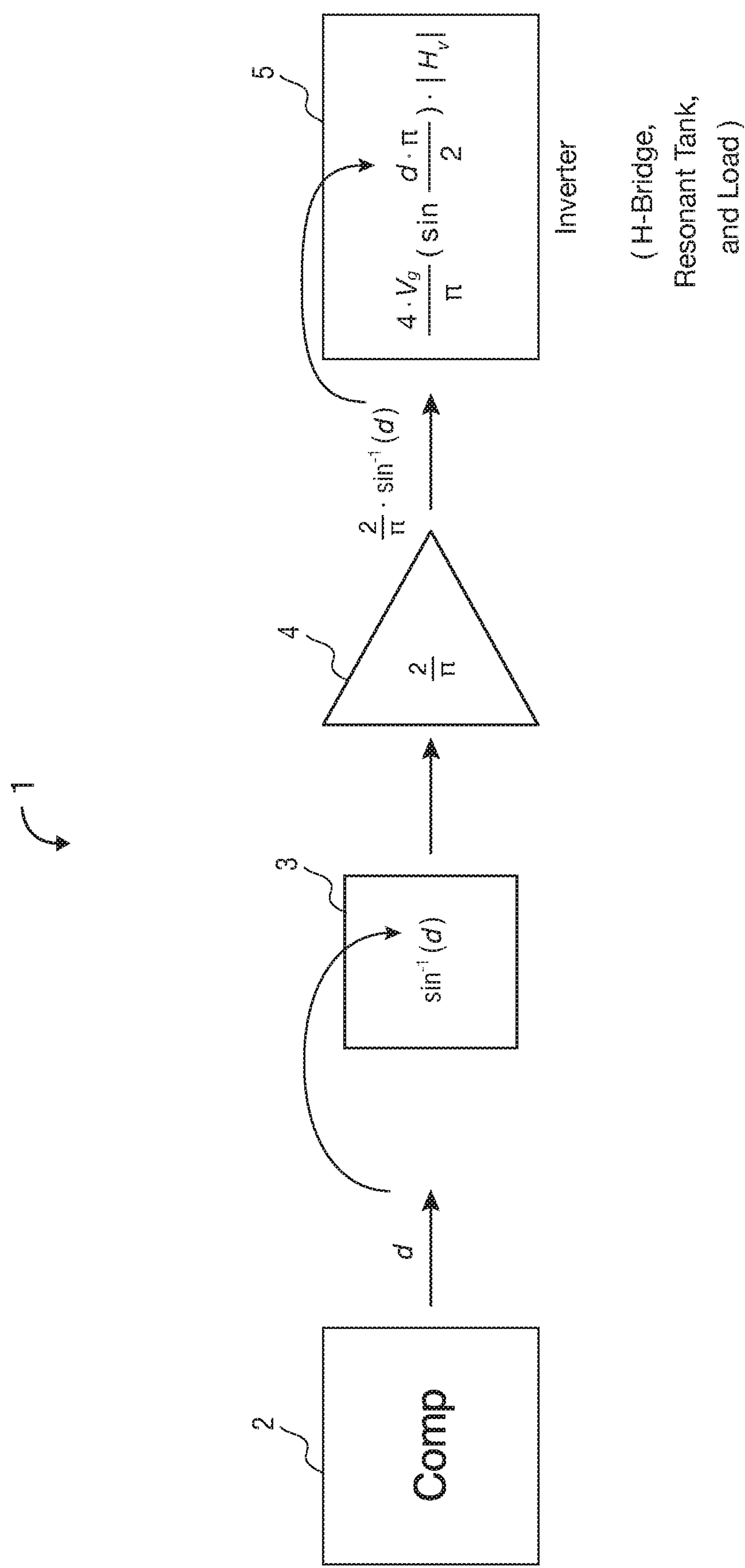
FIG. 3A is a network model of an electrosurgical generator in accordance with the present disclosure in voltage control mode and/or current control mode.

Turning to FIG. 3A, a network model of an electrosurgical generator 1 in accordance with the present disclosure in voltage control mode and/or current control mode is shown. In voltage control mode and current control mode, the variation due to phase is caused by the sine term. To correct for this variation, the phase gain correction function when controlling to voltage and/or current is performed in accordance with an arcsine function. Between the compensator 2 and the inverter 5, an arcsine block 3 and 2/π block 4 is placed. This is because the compensator is outputting duty cycle d (which ranges from 0 to 1) which would then be placed into the sine portion of the output voltage equation, as described in accordance with the formula $$\sin\frac{d\cdot\pi}{2},$$

with $d\cdot\pi=\theta_{12}$. The generator utilizes $$\frac{2}{\pi}\sin^{-1}(d)$$

as the d term of the sine function, which, in turn, results in a duty cycle of $$\sin\left(\frac{2}{pi}\cdot\frac{pi}{2}\sin^{-1}d\right)=d.$$

By this approach, the generator gain is constant with respect to phase in voltage and/or current mode, as the gain would be the derivative of d, not d itself.

Figure 3B:
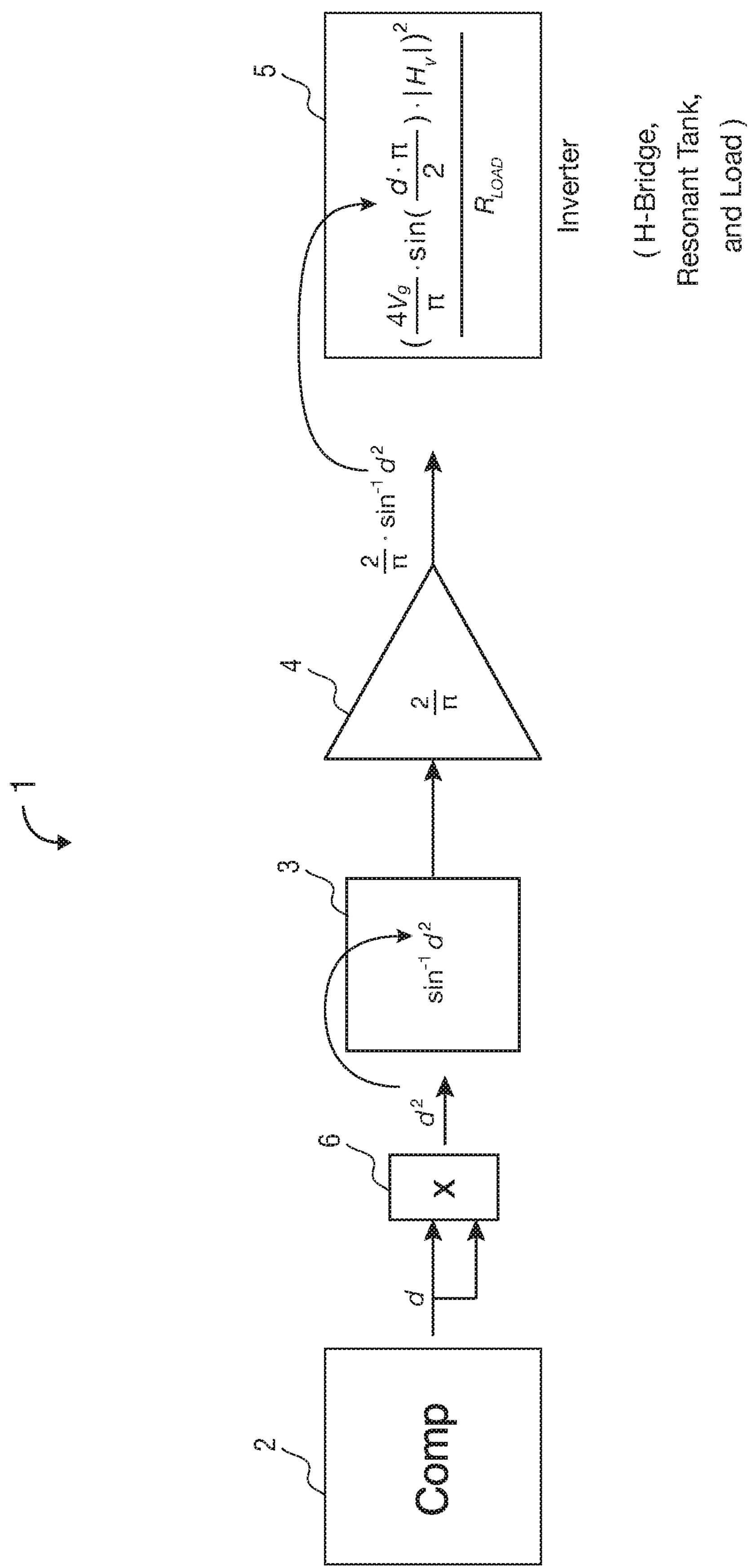
FIG. 3B is a network model of an electrosurgical generator in accordance with the present disclosure in power control mode.

Now with reference to FIG. 3B, a network model of an electrosurgical generator 1 in accordance with the present disclosure in power control mode is shown. In power control mode, the phase gain correction function is performed in accordance with the inverse of a sine squared function. In this model, between the compensator 2 and the arcsine block 3 a multiplier block 6 is placed which computer the square of uncorrected duty cycle d. In turn, the generator utilizes $$\frac{2}{\pi}\sin^{-1}(d^2)$$

as the d term of the sine squared function resulting in a corrected duty cycle of $$\sin^2\left(\frac{2}{pi}\cdot\frac{pi}{2}\cdot\sin^{-1}d^2\right)=d.$$

Again, by this approach the generator gain is constant with respect to phase.

Figure 4:
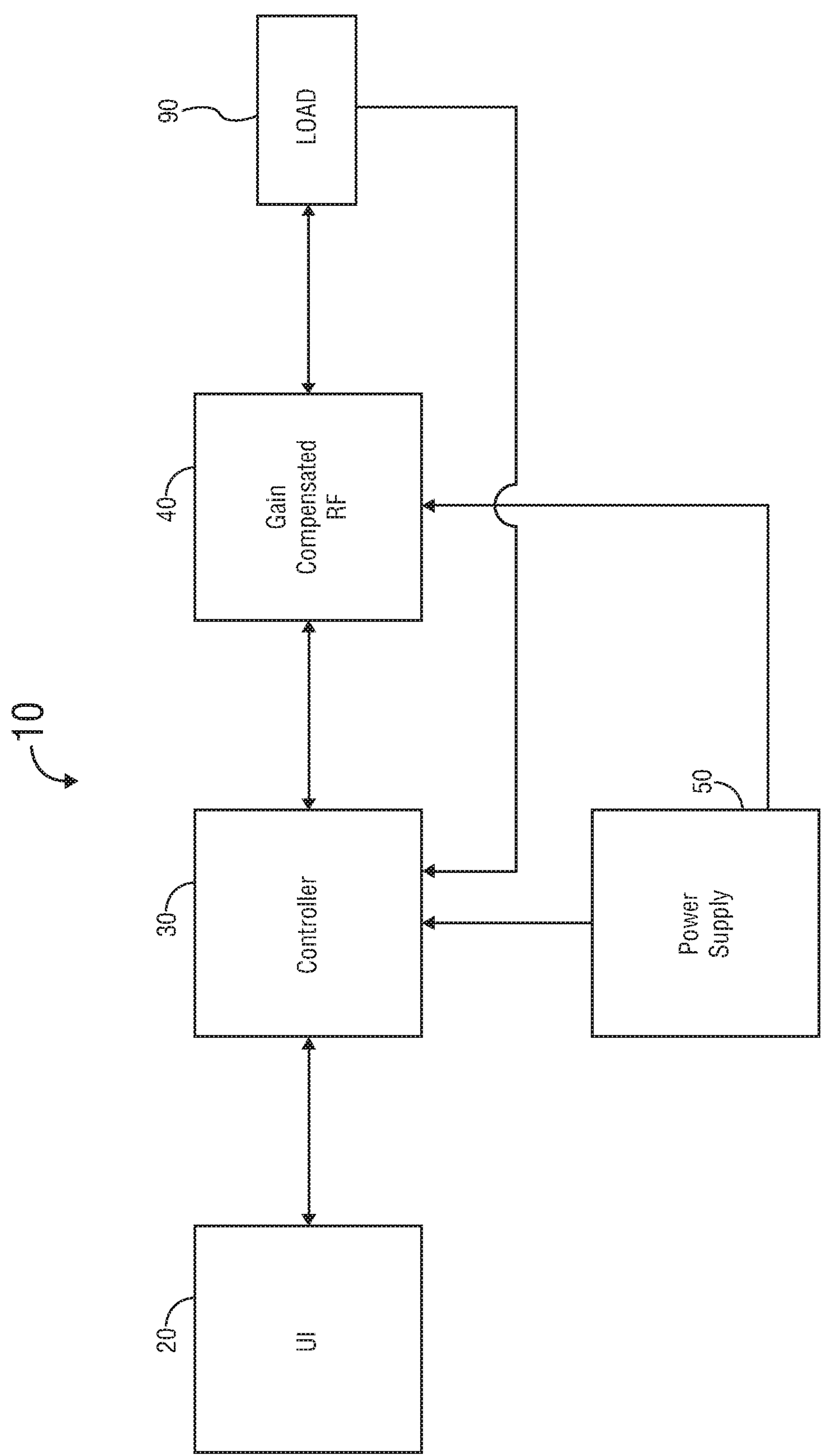
FIG. 4 is a block diagram of an embodiment of a gain-compensated electrosurgical generator in accordance with the present disclosure.

Referring now to FIG. 4, an electrosurgical generator 10 according to the present disclosure is illustrated. In general, the disclosed generator 10 compensates for the underlying cause of gain variations and precisely corrects the variation at the source. By normalizing the gain to a single point that applies across all conditions, not only is stability assured, but the overall control system design is greatly simplified.

The described gain compensation technique is applicable any application utilizing phase shifted full bridge inverter topology. It is simpler than techniques that exist in the prior art and provides a generalized solution that will work across all circuits of this type.

The disclosed generator 10 includes a user interface 20 that is configured to receive inputs from a user that define the operating modes and parameters of the system such as, without limitation, power level, mono- or bi-polar mode, electrosurgical energy on/off, cutting mode, sealing mode, blending mode, coagulation mode, crest factor, and so forth. User interface 20 may include user interface elements such as buttons, knobs, keypads, touchscreens etc. that may be disposed on a generator enclosure and/or on an electrosurgical instrument. User interface 20 may include visual displays and audible indicators to communicate operating status and feedback to a user. Electrosurgical system 10 includes a controller 30 that is in operable communication with user interface 20 and a gain-compensated radiofrequency (RF) stage 40. Controller 30 interprets operating commands received from user interface 20 and, in turn, provides one or more control signals to gain-compensated RF stage 40, such as, without limitation, a setpoint signal. Gain-compensated RF stage 40 may be configured to communicate one or more operating parameters to controller 30, such as, without limitation, an impedance, an output voltage, an output current, and an output power. Gain-compensated RF stage 40 is configured to receive a setpoint signal from controller 30 and, in response thereto, generate an electrosurgical output signal for delivery to a load 90 (e.g., to targeted tissue) in a manner described in detail below. Electrosurgical generator 10 includes a power supply 50 which is configured to convert line voltage (e.g., 120 VAC or 240 VAC) to operating voltages required by user interface 20, controller 30, and gain-compensated RF stage 40. In some embodiments, power supply 50 is configured to provide +5 VDC, −5 VDC, +12 VDC, and +150 VDC.

Figure 5:
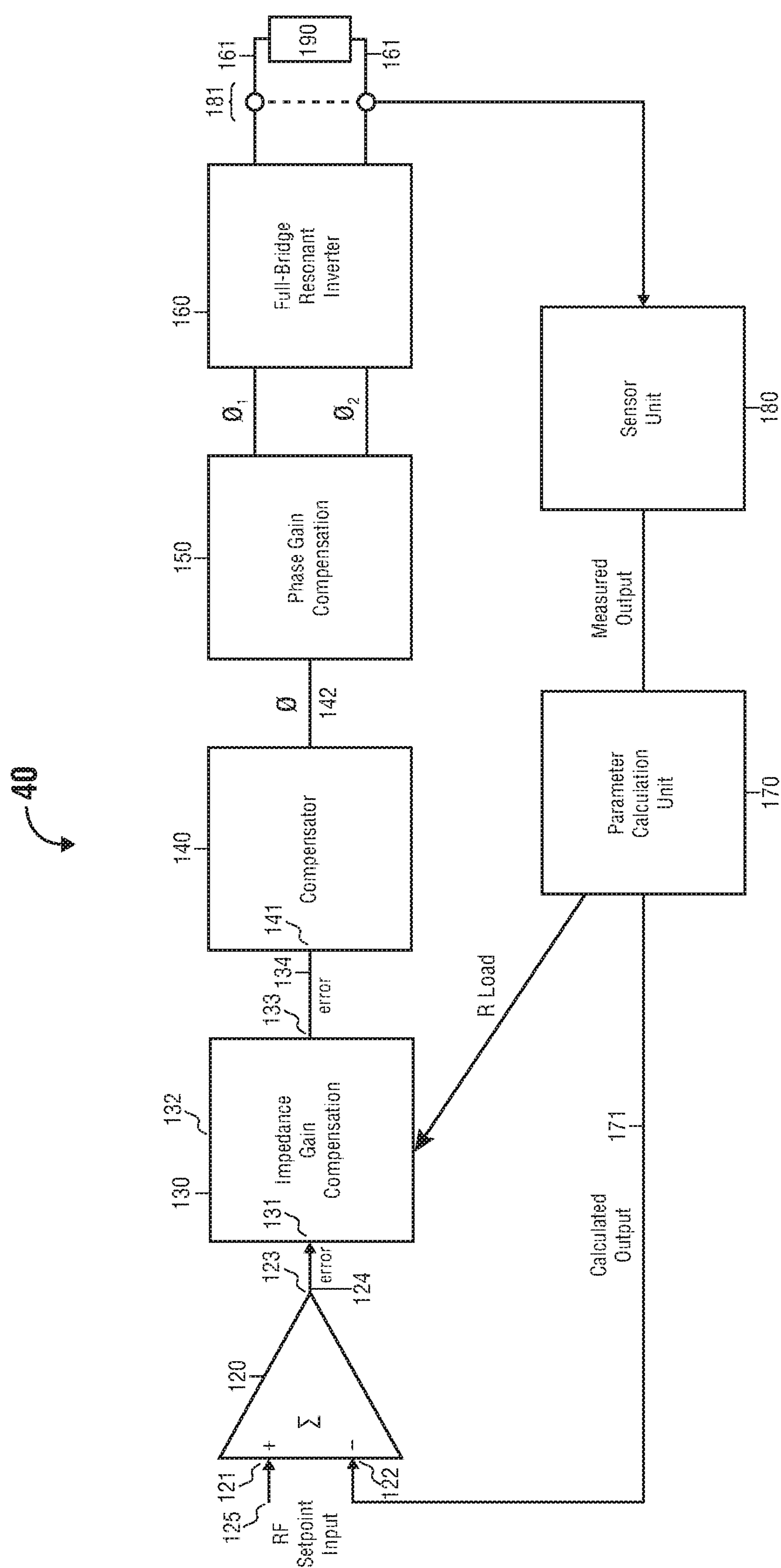
FIG. 5 is a block diagram of an embodiment of a gain-compensated RF stage of an electrosurgical generator in accordance with the present disclosure.
Figure 6:
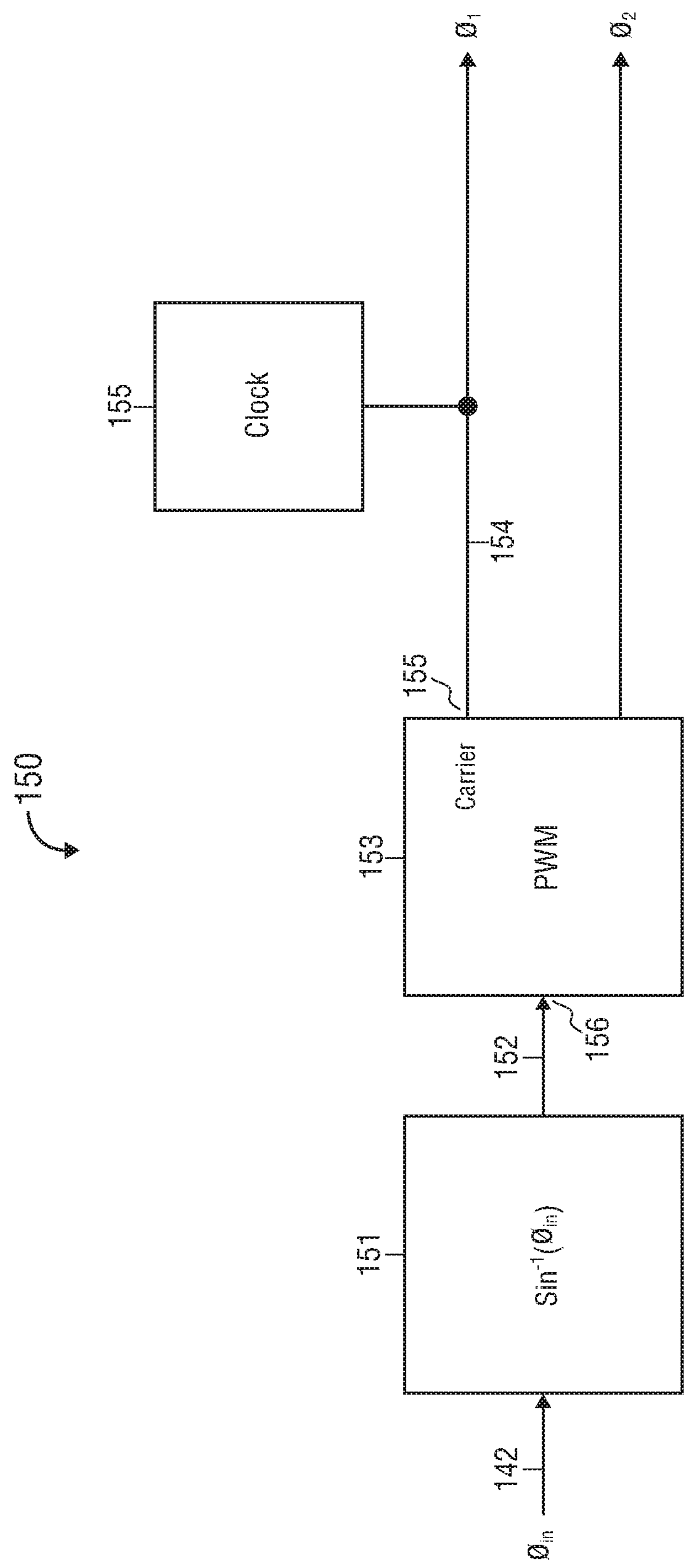
FIG. 6 is a block diagram of a phase gain compensation unit of an electrosurgical generator in accordance with the present disclosure.
Figure 7:
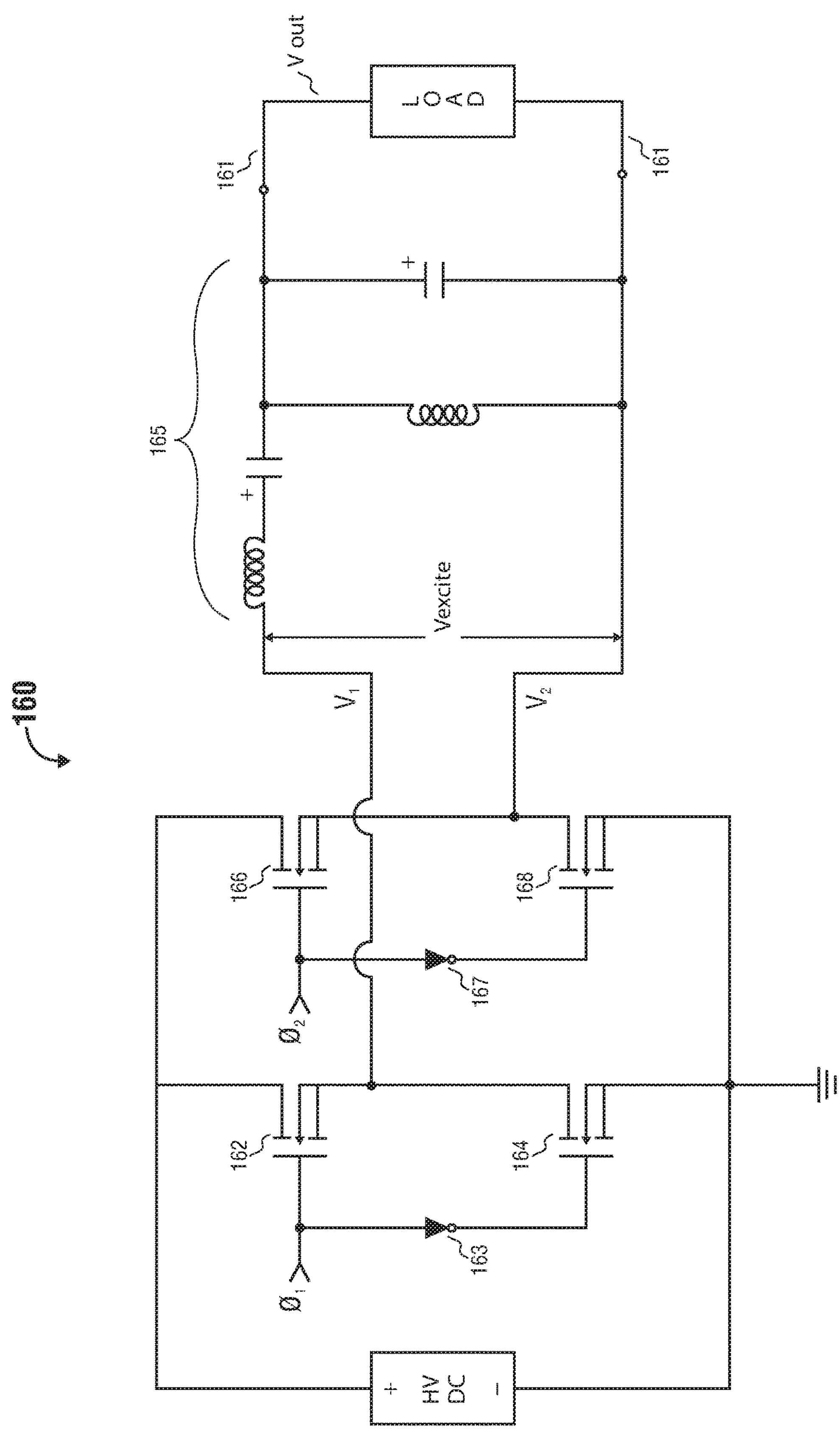
FIG. 7 is a schematic diagram of a full-bridge inverter output stage of an electrosurgical generator in accordance with the present disclosure.
Figures 8A, 8B:
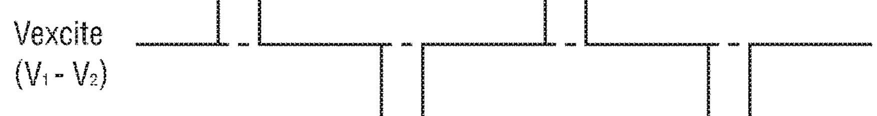
FIGS. 8A-8D illustrate relationships between operating waveforms of a full wave bridge inverter, shown at varying output levels, in accordance with an embodiment of the present disclosure.
Figure 8C:
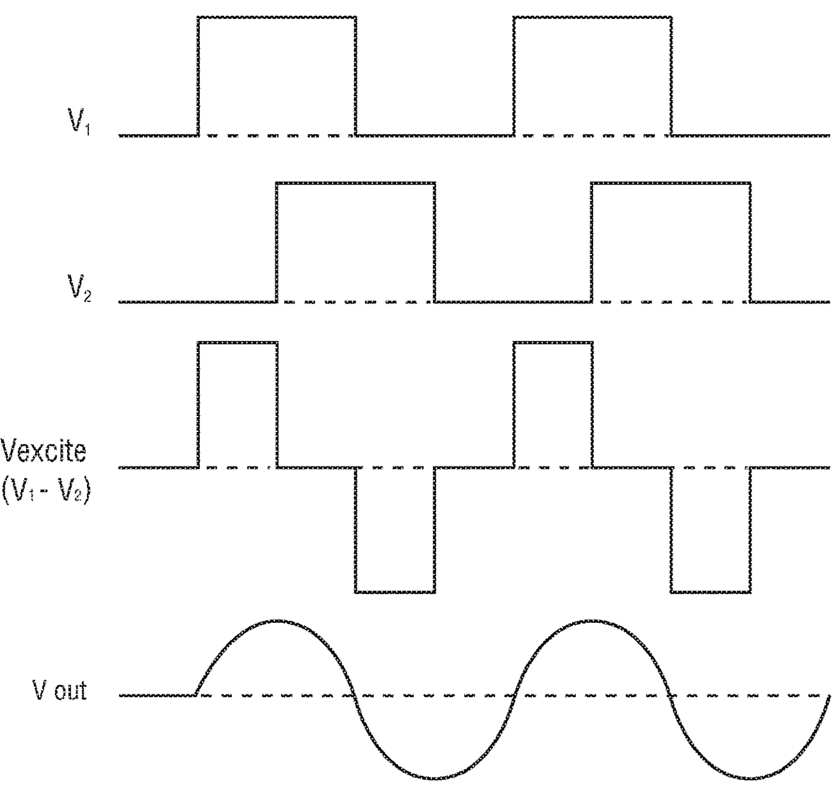
Figure 8D:
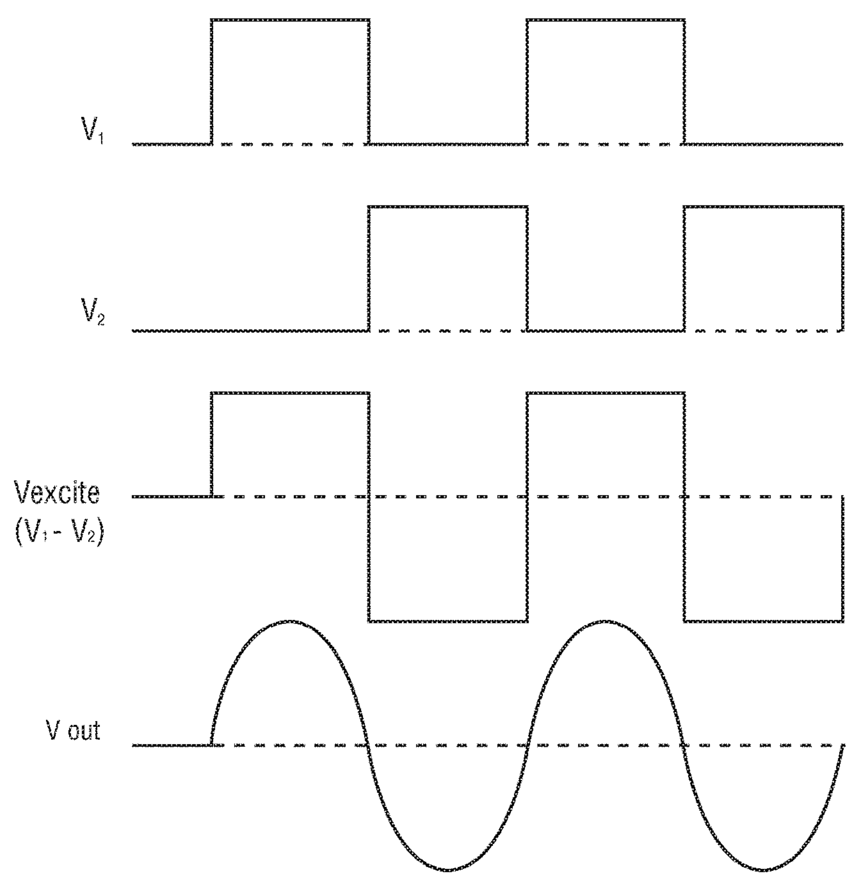

Turning now to FIGS. 5 and 6, a gain-compensated RF stage 40 in accordance with the present disclosure is now described. Gain-compensated RF stage 40 employs a two-part approach to achieving gain compensation. The first approach addresses gain variations caused by load (impedance) variations of a full-bridge resonant inverter output stage 160. The second approach addresses gain variation caused by the sine term of the duty cycle modulation (e.g., pulse width modulation) of the full-bridge resonant inverter output stage 160 during current- and voltage-control modes, and gain variation caused by the sine squared term of the duty cycle modulation during power control modes.

In greater detail, gain-compensated RF stage 40 is generally arranged as an improved control loop having two gain-compensation error-correction elements. A first impedance gain compensation unit 130 is provided prior to the input of a PID section 140, and a phase gain compensation unit 150 is provided subsequent to the PID section 140. Gain-compensated RF stage 40 includes a summation amplifier 120 having an RF setpoint input 121 which receives RF setpoint signal 125 at a positive (+) input of summation amplifier 120. A calculated output signal 171 (e.g., a setpoint "equivalent" corresponding to an output parameter) is received at a negative (−) input of summation amplifier 120. Summation amplifier 120 generates a first error signal 124 at summation amplifier output 123 corresponding to the difference between the RF setpoint signal 125 (e.g., desired output) and the calculated output signal 171 (e.g., actual output). The first error signal 124 which is communicated as the error term to an error input 131 of impedance gain compensation unit 130. In addition to error input 131, impedance gain compensation unit 130 includes load input 132 that is configured to receive a load signal $R_{LOAD}$ from full-bridge resonant inverter 160. As such, impedance gain compensation unit 130 is configured to compensate for load variations of full-bridge resonant inverter 160 in addition to gain variations.

Impedance gain compensation unit 130 is configured to generate second error signal 134 at impedance gain compensation unit output 133 that is communicated to PID controller 140. The compensation required due to load variation is dependent not only on the load, but also on the control method. However, because tissue impedance changes relatively slowly in comparison to the frequency at which the setpoint may be changed, gain compensation based on load is reliably achieved. The load compensation is determined in accordance the gain variation equations listed in Table 1, presented below, wherein Zo0 is the Thevenin equivalent output impedance of the resonant network (e.g., reactive):

TABLE 1

| Voltage | Current | Power |
|---|---|---|
| $\text{abs}\left(\frac{R_{LOAD}}{R_{LOAD}+Z_{o0}}\right)$ | $\text{abs}\left(\frac{1}{R_{LOAD}+Z_{o0}}\right)$ | $\text{abs}\left(\frac{R_{LOAD}}{(R_{LOAD}+Z_{o0})^2}\right)$ |

The reciprocals of the gain variations calculated by the equations of Table 1 generate the error term to be applied to error input 141 of PID controller 140, to effectively normalize the gain due to impedance. The gain compensation equations are presented below in Table 2:

TABLE 2

| Voltage | Current | Power |
|---|---|---|
| $\text{abs}\left(\frac{R_{LOAD}+Z_{o0}}{R_{LOAD}}\right)$ | $\text{abs}\left(\frac{R_{LOAD}+Z_{o0}}{1}\right)$ | $\text{abs}\left(\frac{(R_{LOAD}+Z_{o0})^2}{R_{LOAD}}\right)$ |

Impedance gain compensation unit 130 is programmed to receive the load as a parameter, and adds or removes gain from the system prior to processing by phase gain compensator 150 by preprocessing (e.g., pre-distorting) the error term of the inner control loop in order to compensate for the gain non-linearity due to impedance changes.

PID unit 140 receives error signal 134 from impedance gain compensation unit 130 and generates a phase control signal 142 which determines the duty cycle of a full-bridge inverter driver, e.g., a pulse width modulation unit, included within phase gain compensation unit 150.

With attention now to FIG. 6, phase gain compensation unit 150 receives phase control signal 142. The phase gain compensation unit 150 corrects for the inherent nonlinearity associated with pulse width modulation techniques. In more detail, in prior-art full bridge inverters, a linear increase of the pulse width modulation duty cycle results in an increase in full-bridge inverter peak-to-peak output in accordance with the sine term. For example, varying the PWM duty cycle (by, e.g., varying the phase difference between the two pulse trains) from 0% to 50% results in the output of a full-bridge inverter (to vary from 0% to 70.7% of peak value.

To compensate for this nonlinearity, in embodiments according to the present disclosure the phase gain compensation unit 150 compensates (e.g., pre-processes or pre-distorts) phase control signal 142 by applying a compensation factor that is based at least in part upon the arcsine term to phase control signal 142, which, in turn, generates a corrected PWM driving signal 152. Phase control signal 142 is received by phase preprocessing module 151. Phase preprocessing module 151 applies the arcsine term to phase control signal 142 to generate PWM driving signal 152. A clock 155 provides a square wave 154 having a phase θ1 to a carrier input 155 of PWM driver 153. In embodiments, clock 155 may be integral to and/or included within PWM driver 153. Typically, square wave 154 has a frequency corresponding to the desired electrosurgical frequency, e.g., 470 kHz. The corrected PWM driving signal 152 is applied to a modulation input 156 of PWM driver 153, which generates a phase-shifted, second square wave having a phase θ2. The phase difference between 01 and 02 is determined by PWM driving signal 152. Phase θ1 and phase θ2 are output from phase gain compensation unit 150 to drive full-bridge inverter 160. Thus, the phase difference between 01 and 02 is pre-processed by the arcsine function by phase preprocessing module 151, which precisely compensates for the sine term nonlinearity of the full bridge inverter 160. In this manner, a purely linear response to the PID 140 output is achieved.

Referring to FIGS. 7 and 8A-8D, full-bridge inverter 160 is now described in more detail. The full-bridge inverter 160 includes a plurality of transistors 162, 164, 166, 168 for configured in a full bridge arrangement to generate a pair of output pulse trains $V_1$, $V_2$. Full-bridge inverter 160 receives phase θ1 and phase θ2 outputs from phase gain compensation unit 150 for driving the plurality of transistors 162, 164, 166, 168. The PWM output is coupled to transistor 162, and, shifted 180 degrees by inverter 163, to transistor 164. Similarly, θ2 is coupled to transistor 166, and to transistor 168 via inverter 167. This push-pull topology is used to accomplish voltage conversion from DC to RF at a desired power level determined by the phase difference between phase θ1 and phase θ2.

As the phase difference between PWM drive signals phase θ1 and phase θ2 is varied, the transistor pairs 162, 164 and 166, 168 conduct in accordance with their respective gate signals, at varying times, to deliver a waveform at the specified power. As best shown in FIGS. 7A-7D, the interference between the two phase shifted, high voltage pulse-trains $V_1$ and $V_2$ generates a combined excitation voltage $V_{EXCITE}$. $V_1$ and $V_2$ are thus summed and subsequently filtered by resonant network 165 to provide a smoothed, generally sinusoidal electrosurgical output waveform 161, 161' ($V_{out}$).

One or more sensors 181 are operably associated with outputs 161, 161' and/or load 190. In embodiments, sensor 181 includes a voltage sensor and/or a current sensor. One or more sensor signals from sensor 181 are received at sensor unit 180, which interfaces and converts the raw sensors signals received from sensor 181 into a format suitable for use by parameter calculation unit 170. In embodiments, sensor unit 180 may include an analog to digital (A/D) converter, a buffer, an optoisolator, an amplifier, a temperature compensation device, a filter, and combinations thereof.

Parameter calculation unit 170 receives the one or more sensor signals, and computes a calculated output signal 171 (i.e., a setpoint equivalent parameter) corresponding to the presently-sensed output of full-bridge inverter 160. The calculated output signal 171 is calculated in accordance with a current operating mode of the generator 10. For example, RMS voltage, RMS current, average power, and impedance may be calculated. If the control method of generator 10 is in a voltage-targeted mode, then the present output voltage is calculated by parameter calculation unit and subtracted from the setpoint by summation amplifier 120. If the control method of generator 10 is in a voltage-targeted mode, then the calculated output signal 171 is calculated from the present output voltage. If the control method of generator 10 is in a current-targeted mode, the calculated output signal 171 is calculated from the present output current. Similarly, if the control method of generator 10 is in a power-targeted mode, then present output power is calculated, and if the control method of generator 10 is in an impedance-targeted mode, then the present load impedance is calculated. The calculated output signal 171 is received at the negative (−) input of summation amplifier 120, which sums the setpoint signal 125 with the calculated output signal 171, to generate the error signal 124 used to drive the gain-compensated RF stage 40 as just described.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

The invention claimed is:

1. An electrosurgical generator comprising:
- a summation unit configured to generate an error signal based on a difference between a radio frequency setpoint signal and a calculated output signal;
- a controller configured to generate a phase control signal based on the error signal;
- a phase gain compensation unit including a pulse width modulation driver configured to generate a first driving signal and a second driving signal phase-shifted from the first driving signal based on the phase control signal; and
- a radio frequency inverter configured to generate an electrosurgical output signal based on a selected operating mode and the first driving signal and the second driving signal.

2. The electrosurgical generator according to claim 1, further comprising a sensor circuit configured to sense an electrical property of the electrosurgical output signal and generate the calculated output signal.

3. The electrosurgical generator according claim 2, wherein the sensor circuit comprises:
- a sensor coupled to the radio frequency inverter and configured to output a sensor signal; and
- a parameter calculation unit configured to calculate the calculated output signal.

4. The electrosurgical generator according to claim 3, wherein the controller is configured to calculate an impedance signal corresponding to a load impedance based on the calculated output signal.

5. The electrosurgical generator according to claim 4, further comprising an impedance gain compensation unit configured to modify the error signal based on the impedance signal.

6. The electrosurgical generator according to claim 4, wherein the radio frequency inverter includes a resonant network configured to shape the electrosurgical output signal into a sinusoidal electrosurgical output waveform.

7. The electrosurgical generator according to claim 6, wherein the selected operating mode is a voltage-targeted mode and the controller is configured to calculate the impedance signal according to a formula (I):

$$\mathrm{abs}\left(\frac{R_{LOAD}+Z_{o0}}{R_{LOAD}}\right), \quad \text{(I)}$$

wherein $R_{LOAD}$ is the load impedance and $Z_{o0}$ is a reactive Thevenin equivalent output impedance of the resonant network.

8. The electrosurgical generator according to claim 6, wherein the selected operating mode is a current-targeted mode and the controller is configured to calculate the impedance signal according to a formula (II):

$$\mathrm{abs}\left(\frac{R_{LOAD}+Z_{o0}}{1}\right), \quad \text{(II)}$$

wherein $R_{LOAD}$ is the load impedance and $Z_{o0}$ is a reactive Thevenin equivalent output impedance of the resonant network.

9. The electrosurgical generator according to claim 6, wherein the selected operating mode is a power-targeted mode and the controller is configured to calculate the impedance signal according to a formula (III):

$$\mathrm{abs}\left(\frac{(R_{LOAD}+Z_{o0})^2}{R_{LOAD}}\right), \quad \text{(III)}$$

wherein $R_{LOAD}$ is the load impedance and $Z_{o0}$ is a reactive Thevenin equivalent output impedance of the resonant network.

10. The electrosurgical generator according to claim 1, wherein the phase gain compensation unit further includes a phase preprocessing module configured to modify the phase control signal based on a phase gain correction function.

11. The electrosurgical generator according to claim 10, wherein the phase gain correction function is an arcsine function.

12. The electrosurgical generator according to claim 1, wherein the phase gain compensation unit includes a clock module coupled to the radio frequency inverter and configured to generate the first driving signal.

13. The electrosurgical generator according to claim 1, wherein the selected operating mode of the electrosurgical generator is selected from the group consisting of a voltage-targeted mode, a current-targeted mode, a power-targeted mode, and an impedance-targeted mode.

14. An electrosurgical generator comprising:

a user interface configured to receive a user input from a user;

a first controller configured to receive an operational parameter from the user interface based on the user input and to generate a radio frequency setpoint signal; and a radiofrequency output stage, comprising:

a summation unit configured to generate an error signal based on a difference between the radio frequency setpoint signal and a calculated output signal;

a second controller configured to generate a phase control signal based on the error signal;

a phase gain compensation unit including a pulse width modulation driver configured to generate a first driving signal and a second driving signal based on the phase control signal, the second driving signal being phase-shifted from the first driving signal; and a radio frequency inverter configured to generate an electrosurgical output signal based on a selected operating mode and the first driving signal and the second driving signal.

15. The electrosurgical generator according to claim 14, further comprising a sensor circuit configured to sense an electrical property of the electrosurgical output signal and generate the calculated output signal.

16. The electrosurgical generator according claim 15, wherein the sensor circuit comprises:

a sensor coupled to the radio frequency inverter and configured to output a sensor signal; and a parameter calculation unit configured to calculate the calculated output signal.

17. The electrosurgical generator according to claim 16, wherein the second controller is configured to calculate an impedance signal corresponding to a load impedance based on the calculated output signal.

18. The electrosurgical generator according to claim 17, further comprising an impedance gain compensation unit configured to modify the error signal based on the impedance signal.

19. The electrosurgical generator according to claim 14, wherein the phase gain compensation unit further includes a phase preprocessing module configured to modify the phase control signal based on a phase gain correction function.

20. The electrosurgical generator according to claim 14, wherein the radio frequency inverter includes a resonant network configured to shape the electrosurgical output signal into a sinusoidal electrosurgical output waveform.

* * * * *